United States Patent [19]
Lattin et al.

[11] Patent Number: 5,445,609
[45] Date of Patent: Aug. 29, 1995

[54] ELECTROTRANSPORT AGENT DELIVERY DEVICE HAVING A DISPOSABLE COMPONENT AND A REMOVABLE LINER

[75] Inventors: Gary A. Lattin, Forest Lake; Dale A. Dickson, Fridley; Michael J. Grace, Coon Rapids, all of Minn.

[73] Assignee: ALZA Corporation, Palo Alto, Calif.

[21] Appl. No.: 69,270

[22] Filed: May 28, 1993

[51] Int. Cl.⁶ .............................................. A61N 1/30
[52] U.S. Cl. ........................................ 604/20; 607/149
[58] Field of Search ............... 604/20, 289, 290, 304, 604/307; 607/149, 152; 424/447–449

[56] References Cited

U.S. PATENT DOCUMENTS

| | | | |
|---|---|---|---|
| 4,627,429 | 12/1986 | Tsuk | 128/156 |
| 4,725,263 | 2/1988 | McNichols et al. | 604/20 |
| 4,865,582 | 9/1989 | Sibalis | 607/152 |
| 4,883,457 | 11/1989 | Sibalis | 604/20 |
| 4,942,883 | 7/1990 | Newman | 604/20 |
| 5,037,381 | 8/1991 | Bock et al. | 604/20 |
| 5,053,001 | 10/1991 | Reller et al. | 604/20 |
| 5,128,137 | 7/1992 | Müller et al. | 424/449 |
| 5,135,479 | 8/1992 | Sibalis et al. | 607/152 X |

FOREIGN PATENT DOCUMENTS 9115261 10/1991 WIPO ........................... 604/20

Primary Examiner—C. Fred Rosenbaum
Assistant Examiner—Frank Wilkens III
Attorney, Agent, or Firm—D. Byron Miller; Steven F. Stone; Edward L. Mandell

[57] ABSTRACT

An electrotransport drug delivery device (1) including a reusable component (2), a disposable component (4), and a removable liner (8) temporarily separating the mating surfaces of the components (2,4) during alignment and assembly of the components (2,4). At least one of the components (2,4) has an adhesive mating surface (11) facing the removable liner (8). Also disclosed are a disposable assembly (4) for an electrotransport device (1) and a method for assembling reusable and disposable components (2,4), the components (2,4) of the electrotranport device assembly (1) are adhesively mated.

33 Claims, 8 Drawing Sheets

ELECTROTRANSPORT AGENT DELIVERY DEVICE HAVING A DISPOSABLE COMPONENT AND A REMOVABLE LINER

TECHNICAL FIELD

This invention relates to electrotransport agent delivery devices, and more particularly, to such devices having reusable and disposable parts.

BACKGROUND ART

"Electrotransport" refers generally to the passage of a substance through a substrate, such as skin, mucous membrane, or nails, induced by application of an electrical potential. For example, a beneficial therapeutic agent may be introduced into the human body by electrotransport. One type of electrotransport, electroosmosis, involves the movement of a liquid out of or through a synthetic or biological membrane under the influence of an electric field. A more widely used electrotransport process, iontophoresis, involves the electrically induced transport of charged ions. Another type of electrotransport, electroporation, involves the transport of an agent through transiently-existing pores formed in the substrate under the influence of an electric field. However, in any given electrotransport process, more than one of these processes may be occurring simultaneously to a certain extent.

Accordingly, "electrotransport", as used herein, should be given its broadest possible interpretation so that it includes the electrically induced or enhanced transport of at least one agent, which may be charged, uncharged, or mixtures thereof, regardless of the specific mechanism or mechanisms by which the agent actually is transported.

Electrotransport devices generally use at least two electrodes which are in electrical contact with some portion of the skin, nails, mucous membrane, or other surface of the body. One electrode, commonly referred to as the "donor" or "active" electrode, is the electrode from which the agent is delivered into the body. The other electrode, typically termed the "counter" or "return" electrode, serves to close the electrical circuit through the body. For example, an agent to be delivered is positively charged, i.e. a cation, then the anode will be the active or donor electrode, while the cathode serves to complete the circuit. Alternatively, if an agent is negatively charged, i.e. an anion, the cathode will be the donor electrode. Additionally, both the anode and cathode may be considered donor electrodes if both anionic and cationic agent ions are to be delivered.

Furthermore, electrotransport delivery devices generally require at least one reservoir or source of the agent to be delivered to the body. Examples of such donor reservoirs include a pouch or cavity as described in Jacobsen, U.S. Pat. No. 4,250,878, a porous sponge or pad as disclosed in Jacobsen et al, U.S. Pat. No. 4,141,359, and a pre-formed gel body as described in Webster, U.S. Pat. No. 4,383,529, which are herein incorporated by reference. Such donor reservoirs are electrically connected to, and positioned between, the anode or cathode and the body surface, to provide a fixed or renewable source of one or more agents or drugs. In addition, electrotransport delivery devices have an electrical power source, some having an electrical controller designed to regulate the rate of drug delivery. Other optional elements include rate-controlling membranes, insulating members, and protective backing members.

Since the individual elements in an electrotransport device may have differing life cycles, electrotransport devices may be designed to be distributed in two general components, one being a disposable component and the other being a reusable component. For example, the drug or other beneficial agent contained in the donor reservoir may be depleted long before the completion of the useful life of certain hardware used in the device such as the power source or electrical controller. In this case, the disposable component may contain an agent reservoir and the reusable component may contain an electrical controller component and/or an electrical power source. In another example, the power source may be a battery having a limited life cycle, while the electrical controller contains long-lasting solid state circuitry. Here, the battery may be placed in the disposable component, while the electrical controller is placed in the reusable component. Although there are numerous element combinations which may be envisioned in each of the disposable and reusable components, a "reusable component", as that term is used herein, refers to one component of a electrotransport device whose useful life exceeds that of a second component, referred to herein as a "disposable component", wherein the two components may be separated so that the reusable component may subsequently be reused while the disposable component is discarded and replaced with another disposable component. In general, the reusable and disposable components are mated to one another, by mechanical and/or electrical connections, in order to form a complete electrotransport device, which device is then adapted to be placed in agent transmitting relation with the body surface (e.g., skin or mucosal membrane) of a patient. Exemplary of electrotransport delivery devices having reusable and disposable components are those disclosed in U.S. Pat. Nos. 4,865,582; 4,950,229 (see column 8, lines 38–40); and 5,037,381.

U.S. Pat. No. 4,865,582 (Sibalis) discloses as electrically powered transdermal drug applicator having a reusable power supply and a disposable drug reservoir. In one embodiment (see FIG. 2A), the drug reservoir has an adherent surface 13 which presumably has a release liner (similar to liner 48) affixed thereto prior to device assembly. In order to assemble the device, the end user peels off the release liner, then applies the adherent surface of the disposable drug reservoir to the reusable power supply/controller 54. The release liner is intended to mask or protect the adhesive prior to assembly of the device and is removed prior to alignment of the reusable and disposable components. Unfortunately it is sometimes difficult to precisely align the controller 54 with the disposable component during mating of the two components. This problem is exacerbated by the adhesive 13 which can cause the disposable and reusable components to mate in a misaligned configuration. Hence, misalignment and premature adhesion of the components may occur with this device assembly. Realignment after premature adhesion is aggravating to the end user, at a minimum, and may also cause damage to the adhesive or drug reservoir.

In order to assemble an electrotransport device having two components designed to be adhesively mated, with or without other mechanical connectors, the user must align the reusable component to the disposable component and optionally make the appropriate mechanical and/or electrical connections. The devices of the prior electrotransport art are prone to misalignment of the reusable and disposable components. This misalignment is difficult, if not impossible to correct, particularly once the misaligned components have become adhesively bonded together. This misalignment of components can adversely affect the operation of the assembled electrotransport device.

DISCLOSURE OF THE INVENTION

Accordingly, it is an object of the present invention to provide an electrotransport device having reusable and disposable components adapted to be adhesively mated, the alignment of which can be easily adjusted after the components have been brought in contact with one another.

It is another object of this invention to improve the precision and accuracy of the alignment of the reusable and disposable components of an electrotransport device.

It is another object of this invention to provide for the alignment of the reusable and disposable components of an electrotransport device prior to adhesive mating of the components to one another.

A further object of this invention to provide for the mechanical and electrical connection of the reusable and disposable components of an electrotransport device prior to adhesive mating of the components to one another.

Yet another object of this invention is to provide a method of preventing premature adhesion of two components of an electrotransport device during alignment of the components.

The electrotransport device of this invention which achieves these objects comprises two components which must be aligned and mated to one another prior to initiation of agent delivery. One component is a reusable component, preferably containing a power source and associated control circuitry. The other component is a disposable component which preferably includes the beneficial agent to be delivered. The disposable and reusable components have surfaces adapted to mate with and adhere to one another in a plurality of mating orientations, at least one of which is the desired mating orientation. At least one of the components has a mating surface having adhesive properties. Preferably, the disposable component has the adhesive mating surface. Means are provided for aligning the reusable and disposable components in the desired mating orientation. An adhesive release liner is disposed on the adhesive mating surface. The liner prevents the mating surfaces from adhering to one another during alignment of the components. Once the components are aligned in the desired mating orientation, the liner is interposed between the mating surfaces. The liner is readily manually removable from this interposed position in order to permit adhesive mating of the components in the desired mating orientation. Preferably, one or more mechanical connectors are provided both for mechanically connecting the components. Most preferably, the mechanical connection also serves to electrically connect the components. Thus, the invention provides a means of accurately and precisely aligning and securely mating two components of an electrotransport drug delivery device to one another.

The above-described objects of our invention and the many advantages associated therewith will be readily apparent from the following description of our invention with reference to the accompanying drawings.

BRIEF DESCRIPTION OF THE DRAWINGS

This invention will be described in further detail with reference to the accompanying drawings wherein.

MODES FOR CARRYING OUT THE INVENTION

Figure 1:
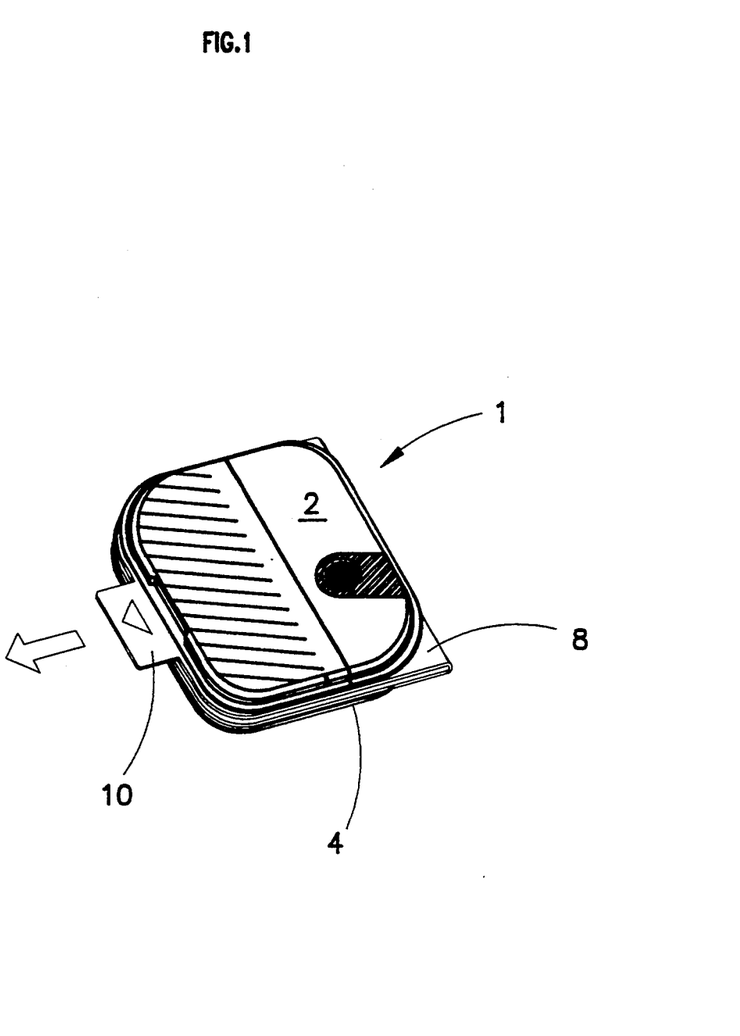
FIG. 1 is a perspective view of one embodiment of the electrotransport device after connection of the reusable and disposable components and prior to removal of the removable liner.
Figure 2:
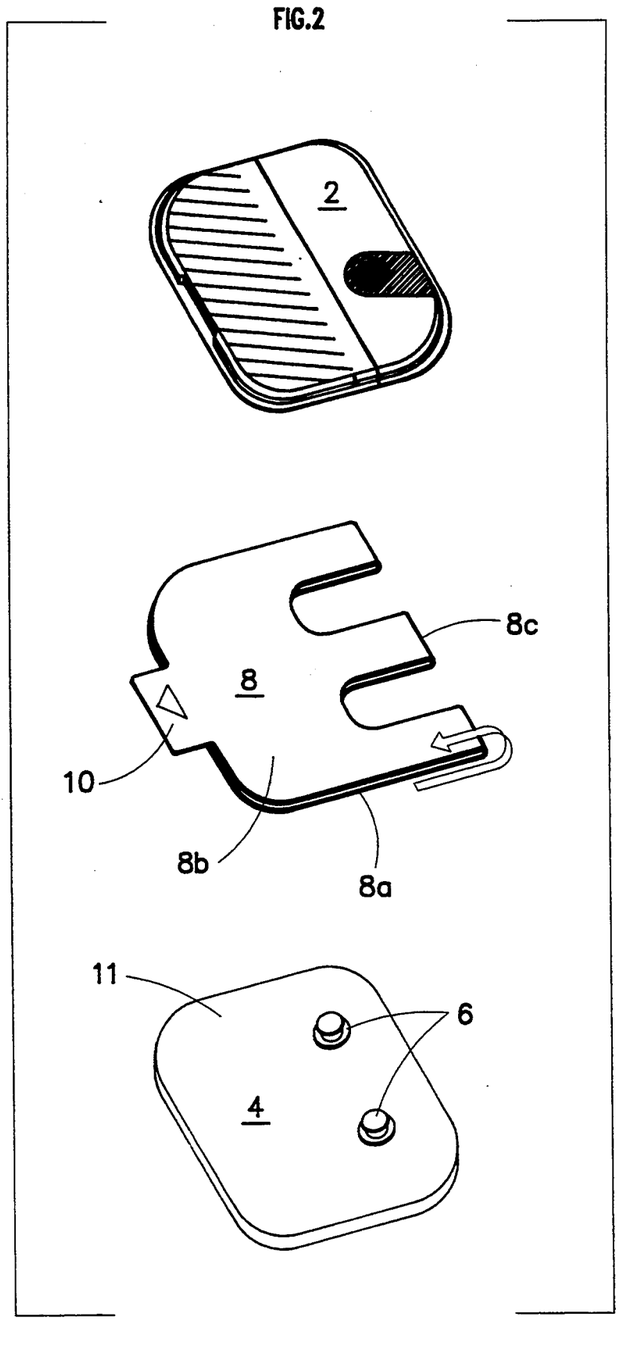
FIG. 2 is an exploded view of the device of FIG. 1.

Referring now to the drawings, FIGS. 1 and 2 illustrate one embodiment of an electrotransport device 1 of this invention. Device 1 comprises a reusable component 2, a disposable component 4 and a removable liner 8 disposed therebetween. Reusable component 2 preferably contains the electric power source and related control circuitry, while disposable component 4 preferably contains donor and counter electrodes and reservoirs, as shown more clearly in FIG. 7. The mating surface of one of the components, preferably the disposable component, is adhesive so that the two components can be releasably bonded together after removal of the liner, as described in detail below. Further, the adhesive surface allows liner 8 to be releasably affixed on the disposable component during shipment of the component and assembly of the device.

As can be seen in both FIGS. 1 and 2, the size and shape of the peripheral edge of component 2 is approximately the same as the size and shape of the peripheral edge of component 4. The components 2 and 4 are designed to be adhesively mated to one another with their respective peripheral edges in alignment, as best shown in FIG. 1. Thus, FIG. 1 shows components 2 and 4 in their desired mating orientation. Device 1 is provided with a means for aligning the components 2 and 4 in the desired mating orientation. As best shown in FIG.

2, the means for aligning components 2 and 4 are, in device 1, snap connectors. However, those skilled in the art will readily appreciate that other conventional forms of alignment means may be used in place of snap connectors 6.

The device is assembled by connecting the reusable component 2 and disposable component 4, to which liner 8 is releasably engaged, by joining male snap connectors 6 on component 4 to female snap connectors (not shown) on the underside of component 2. Access means 7 (see FIG. 3) are provided in liner 8 to permit: (a) the male snap connectors 6 to be snapped into their female counterparts with the liner 8 interposed between the components 2 and 4; and (b) the liner 8 to be removed without disturbing the snap connectors 6. Preferably, the aligning means also provides an initial mechanical connection and an electrical connection of the components 2 and 4. Snap connections 6 provide at least the additional function of mechanically connecting components 2 and 4, and in cases where the snap connectors 6 are composed of an electrically conductive material (e.g., metal or metal coated snap connectors), they provide both additional functions.

The liner 8 comprises a sheet of material folded over on itself at fold axis 8c to provide a first sheet portion 8a releasably adhered to the adherent mating surface 11 of component 4 and a second sheet portion 8b adjacent to component 2. The sheet should have a relatively low coefficient of friction to permit it to slide easily when pulled in the direction of the arrow in FIG. 2 by means of grasping means 10 on one of the ends of liner 8 opposite fold axis 8c. Access means in this embodiment are essentially parallel slots in the liner 8 which traverse fold axis 8c and are aligned with snap connectors 6 so that liner 8 does not interfere with the operation of snap connectors 6.

Preferably the sheet portion 8b having grasping means 10 does not contact the component having the adhesive mating surface (i.e., surface 11). In this manner, sheet portion 8b slides along a non-adhesive mating surface, as opposed to encountering substantially greater resistance by sliding along an adhesive mating surface. Thus, orienting liner 8 such that grasping means 10 is not adjacent the adhesive surface 11 minimizes the force required to extract liner 8 after alignment and initial connection of the components 2 and 4. Such an orientation benefits the patient or assembler of the device by reducing the difficulty of assembly.

Snap connectors 6 align and mechanically connect the components 2 and 4 of the device in their desired mating orientation alignment, as shown in FIG. 1. After this initial mechanical connection has been achieved, liner 8 is removed by pulling on grasping menas 10 in the direction of the arrow. This causes first surface 8a to unroll or peel from the adhesive mating surface 11 of component 4 by means of a tensile force acting essentially normal to surface 11 at the fold axis 8c, both initially and as the fold traverses the surface 11 of component 4. Thus, the force required to remove liner 8 is significantly less than the shear force, acting parallel to the adhesive surface 11, that would be required to overcome the bond connecting liner 8 to component 4 over their entire contacting surfaces if liner 8 was in the form of a single sheet and was pulled in the direction of the arrow. The slots 7 are located such that fold axis 8c in the liner 8 is not impeded, by interaction with snap connectors 6, from traversing easily across the surfaces of components 2 and 4 as the liner 8 is pulled in the direction of the arrow in FIG. 2.

Figure 3:
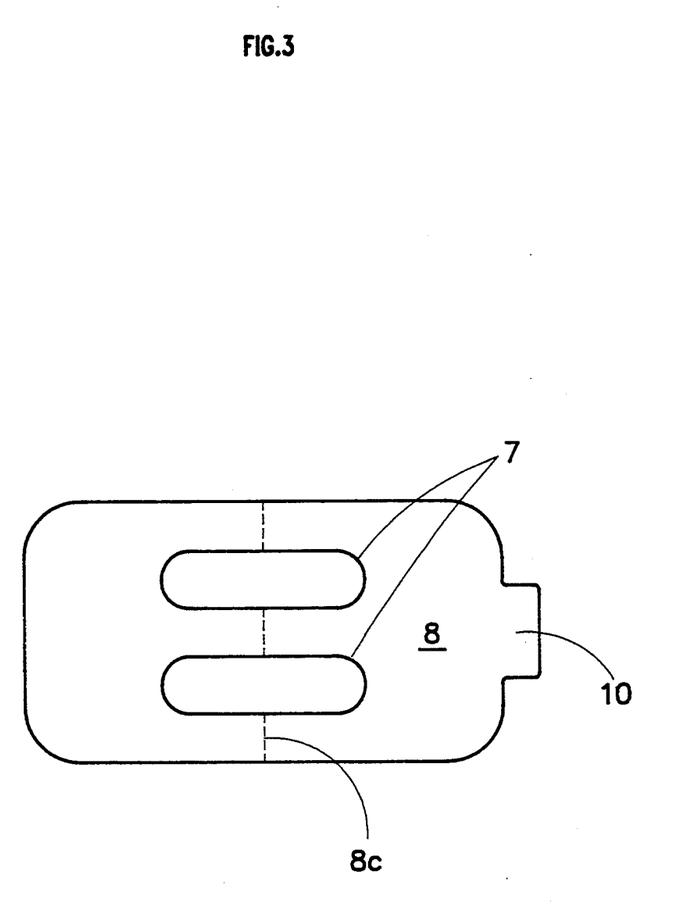
FIG. 3 is a plan view of the removable liner of FIG. 1 in an unfolded position.
Figure 4:
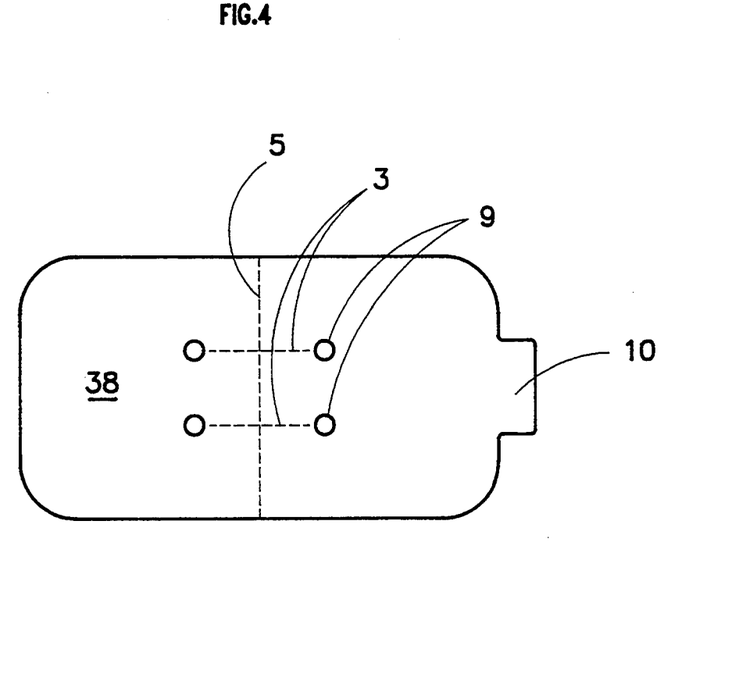
FIG. 4 is a plan view of another embodiment of the removable liner of this invention in an unfolded position.
Figure 5:
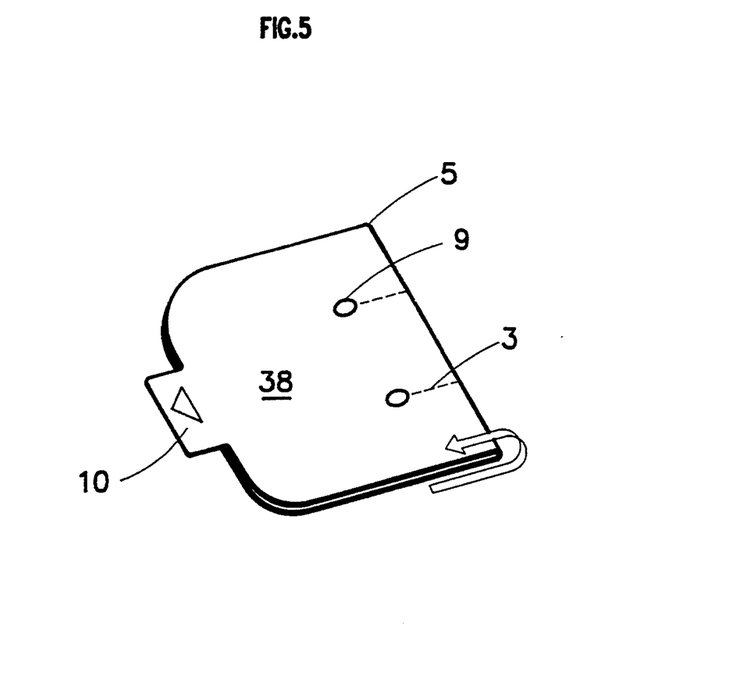
FIG. 5 is a perspective view of the removable liner of FIG. 4 in a folded position.

In cases where the means for aligning components 2 and 4 also provide a mechanical connection, an electrical connection, or both, it is usually necessary for the mechanical and/or electrical connectors to extend through the removable liner. Hence, the liner is preferably formed such that connectors may pass through the folded position of the liner. Although numerous designs may be envisioned by a person having ordinary skill in the art, FIGS. 2-5 illustrate two preferred embodiments according to the present invention. Both FIGS. 3 and 4 depict a plan view of a removable liner in an extended position, while FIGS. 2 and 5 illustrate corresponding folded positions of the same two liners, respectively.

FIGS. 2 and 3 show an embodiment wherein a removable liner 8 has two elongated slots 7 therethrough. These elongated slots 7 are provided for mechanical-/electrical connectors 6 which extend from disposable component 4 to reusable component 2 when the electrotransport device is assembled (See FIG. 1 for assembly). This design permits the liner to be pulled past the joined snap connectors 6 after alignment of components 2 and 4 is achieved.

Alternatively, FIGS. 4 and 5 depict another embodiment wherein a removable liner 38 has four circular holes 9 therethrough. Holes directly opposite each other, separated by the fold axis 5, have perforations 3 extending between them. The term "perforations", as used herein, refer both (1) to a continuous cut through the liner and (2) to alternating cut and uncut portions through the liner. The perforations 3 aid in preventing tearing of liner 38 during removal thereof from a position interposed between the aligned reusable and disposable components of the electrotransport device. An advantage of this embodiment, as with the elongated slot design of FIG. 2 and 3, is that the liner 38 may be easily pulled past the snap connectors 6 after alignment of components 2 and 4.

Once the male portions of snap connectors 6 have been joined to their female counterparts, thereby aligning the components 2 and 4 in their desired mating orientation, the liner 8 may be removed in order to effectively mate components 2 and 4. The removable liner 8 is removed by manually grasping and pulling the portion of the liner extending beyond the edges of the disposable and reusable components, on the side opposite the liner perforations or cuts. This extended liner portion is herein termed a grasping means 10, as shown in FIG. 2. The grasping means 10 preferably extends an adequate distance beyond both components 2 and 4 such that grasping with the user's fingers may be comfortably achievable. Preferably, the grasping means 10 extends from about 6 mm to about 76 mm beyond the peripheral edge of aligned components 2 and 4. More preferably, the tab 10 extends from about 10 mm to about 25 mm beyond component 2 and 4. Upon removal of liner 8, the adhesive coating, preferably only on disposable component 4, provides a further means of mechanically securing the components to one another.

Figure 6:
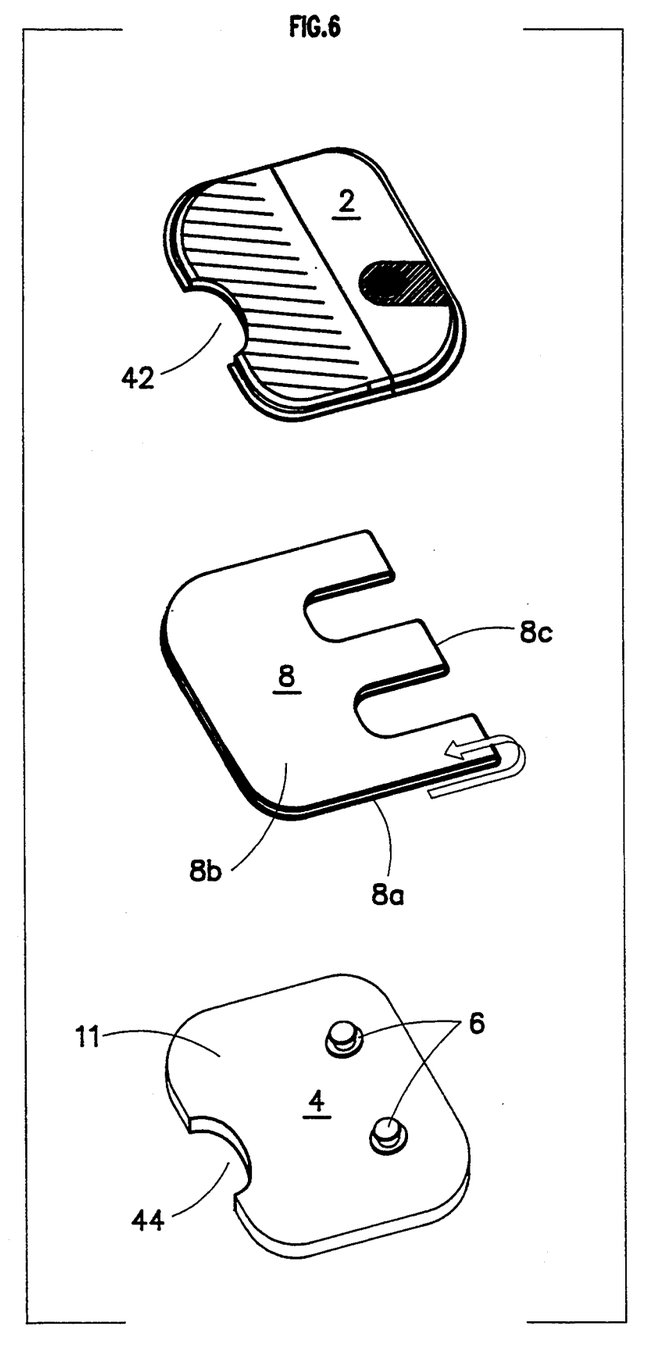
FIG. 6 is an exploded perspective view of one embodiment of an electrotransport device of this invention wherein the reusable and disposable components have corresponding indentations permitting exposure of a grasping means on the removable liner.

In another embodiment, as shown in FIG. 6, both the reusable component 2 has an indentation 42 and the disposable component 4 has an indentation 44 in their peripheral edge which aligns with the edge of liner 8 which is opposite the fold axis 8c. The indentations are located such that they are substantially aligned when the device is assembled. These indentations provide manual access to an exposed portion of the liner 8, i.e.

another form of a grasping means 10. This alignment of indentations enables the user to more readily grasp the liner for removal purposes. However, the electrotransport device may be designed such that only one of the components 2 or 4 has an indentation exposing a portion of liner 8. The salient feature of this embodiment is that the liner 8 have a sufficient portion exposed so as to allow grasping of the liner for removal purposes.

Figure 7:
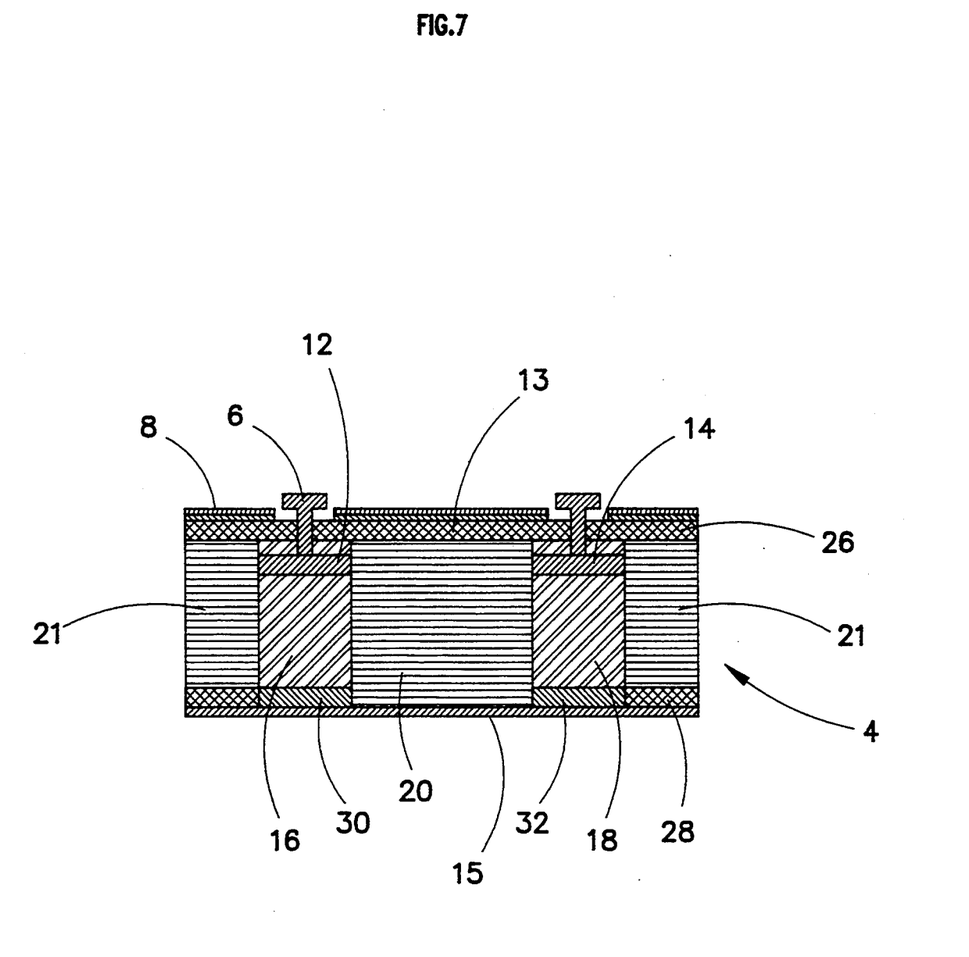
FIG. 7 is a cross sectional view of one embodiment of a disposable section of the present invention.

FIG. 7 is a cross sectional view of one embodiment of a disposable component 4. In this embodiment, the snap connectorss 6 are composed of an electrically conductive material, and hence connectors 6 serve not only as the means for aligning the disposable component 4 in the desired mating orientation but also serve to (i) initially (i.e., just prior to mating) mechanically connect the disposable component 4 to the reusable component 2; and (ii) electrically connect the electrodes 12 and 14 and the reservoirs 16 and 18 to the source of electrical power (e.g., one or more batteries) in the reusable component 2. Male portions of snap connectors 6 conduct current from the power source (not shown) to donor and counter electrodes 12 and 14, respectively. The donor and counter electrodes 12 and 14 are electrically connected to donor and counter reservoirs 16 and 18, respectively. The donor electrode 12 and donor reservoir 16 are insulated from the counter electrode 14 and counter reservoir 18 by insulation 20 disposed therebetween. The electrodes and reservoirs are further insulated from the surroundings by peripheral insulation 21. Rate controlling membranes 30 and 32, such as disclosed in U.S. Pat. No. 5,080,646, can optionally be used to control the flux of donor and counter agents from the reservoirs 16 and 18. Adhesive surface 26 is provided for releasably affixing the disposable component 4 to the reusable component 2 as shown in FIG. 2. Removable liner 8 of the present invention is positioned on adhesive surface 26, thereby covering substantially all of the adhesive surface 26. Peripheral adhesive coating 28 on the skin contacting side of component 4 provides means by which the disposable component may be affixed to a body surface. Suitable self-adhering materials include, without limitation, poly(styrenebutadiene) and poly(styrene-isoprene-styrene) block copolymers, and polyisobutylene copolymers. Other suitable self-adhering matrix materials are set forth in the art such as are described in U.S. Pat. Nos. 4,391,278, 4,474,570, and 4,702,732, all of which are incorporated herein by reference. A second release liner 15 is preferably positioned adjacent adhesive surface 28, in order to isolate the adhesive coating 28 during shipping and handling of disposable component 4.

Figure 8A:
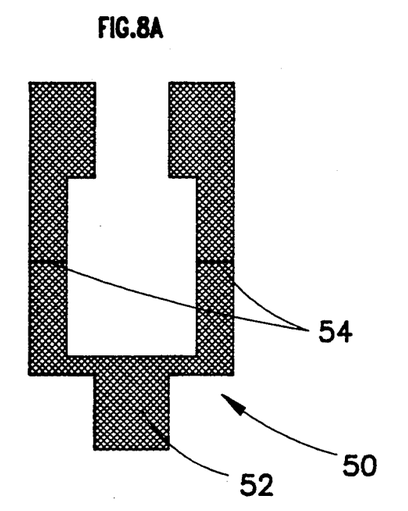
FIG. 8A is a plan view of one component of a two-piece removable liner embodiment in the unfolded position.
Figure 8B:
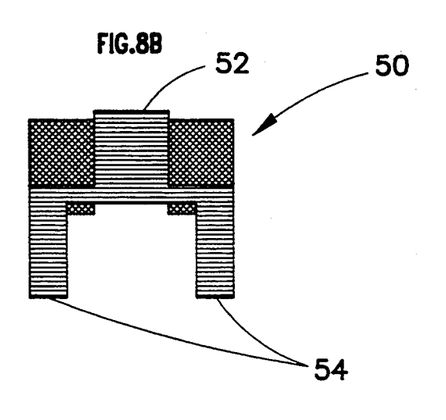
FIG. 8B is a plan view of the FIG. 8A component in a folded position.
Figure 9A:
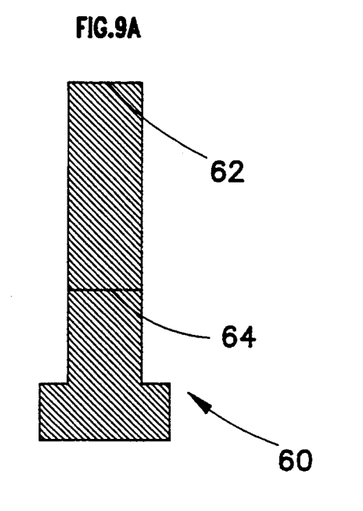
FIG. 9A is a plan view of a second component of a two-piece removable liner embodiment in the unfolded position.
Figure 9B:
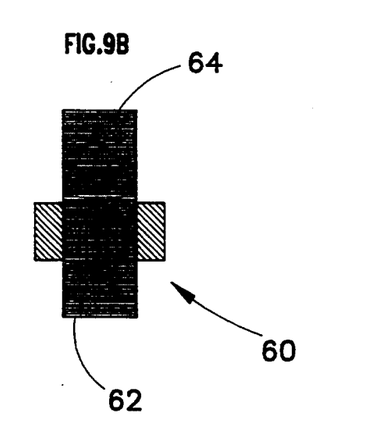
FIG. 9B is a plan view of the FIG. 9A component in a folded position.
Figure 10:
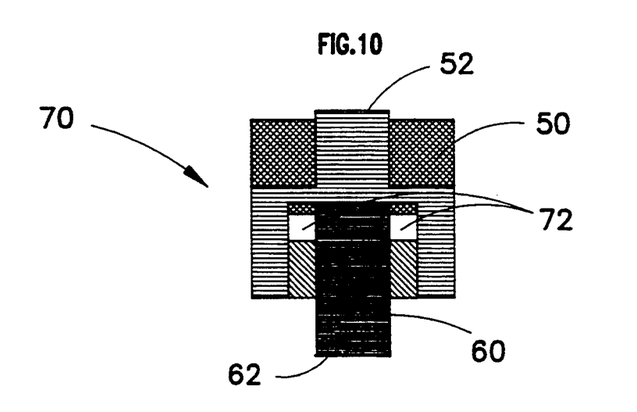
FIG. 10 is a plan view of the assembled two-piece removable liner assembly incorporating FIGS. 9B and 8B liners.

FIGS. 8–10 illustrate another embodiment of the present invention wherein two folded removable liners form a removable liner assembly 70. Unfolded liners 50 and 60 are shown in FIGS. 8A and 9A, respectively. Prior to use, liners 50 and 60 are folded at a fold axes 54 and 64, respectively, as shown in FIGS. 8B and 9B. The folded liners are assembled into the removable liner assembly 70, as shown in FIG. 10, which is configured such that access openings 72 are formed through which the alignment means, and optionally mechanical and/or electrical connectors, on the disposable and/or reusable components may pass. Grasping means 52 and 62 are preferably positioned opposite each other in the assembled 2-piece removable liner 70, as shown in FIG. 10.

Figure 11:
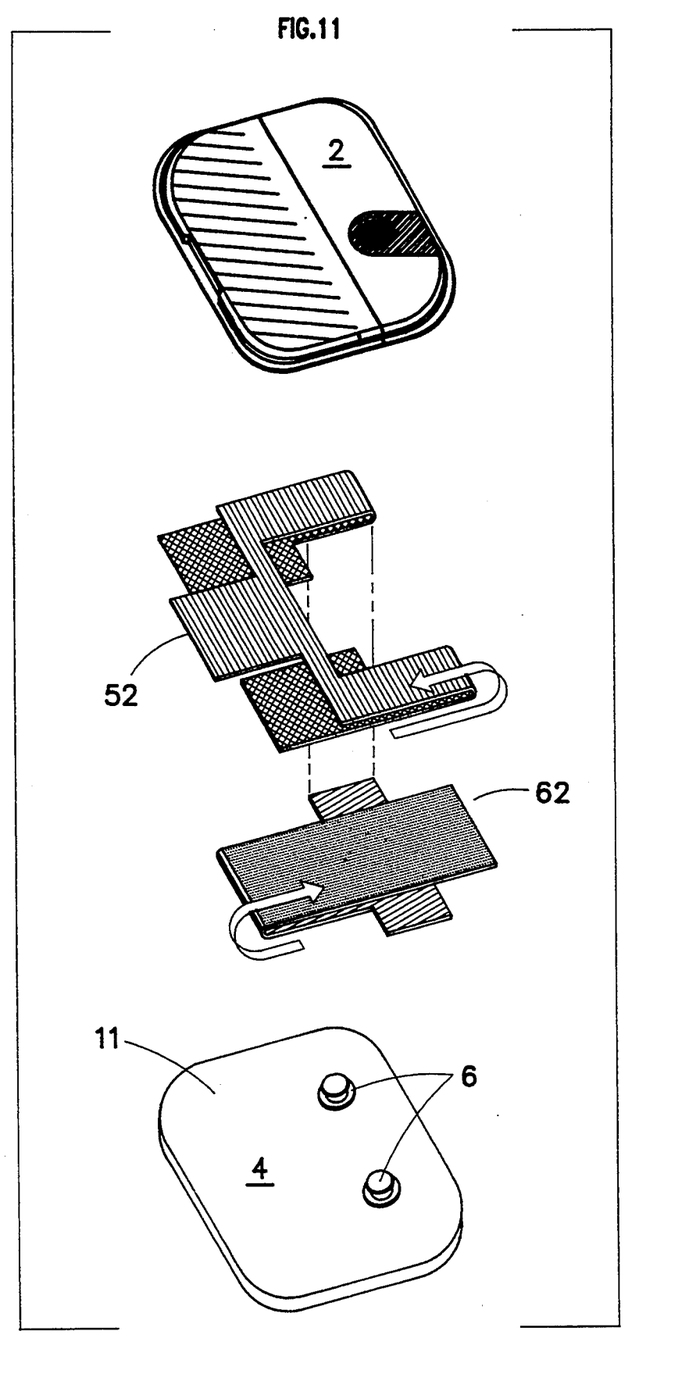
FIG. 11 is an exploded perspective view of one embodiment of the electrotransport device having the two-piece removable liner of FIG. 10.

FIG. 11 is an exploded perspective view of an embodiment of the electrotransport device of this invention having the two-piece removable liner assembly of FIG. 10. The device is assembled by first aligning removable liners 50 and 60 such that access openings 72 provide sufficient space for passing the male portions of the snap connectors 6 on the disposable component 4 therethrough for affixation to mating aligning and connecting means (not shown) on the underside of reusable component 2. Once aligning and connecting means have established alignment and initial mechanical connection of the components, the two removable liners 50 and 60 may be extracted by pulling grasping means 52 in the direction of the upper arrow, and then pulling grasping means 62 in the direction of the lower arrow. Preferably, disposable component 4 is provided an adhesive mating surface 11 and the removable liners 50 and 60 affixed thereto. A skin contact adhesive is preferably also provided on the skin contacting surface of disposable component 4, which adhesive is also preferably protected by a removable liner (not shown in FIG. 11).

The removable liner is preferably coated on at least one surface with a release coating, which allows only weak adhesive forces between the liner and the adhesive coating. A wide variety of release coatings may be used, including without limitation, polymer coatings, waxes, and silicones. Release coating compositions and methods of applying release coatings which are useful with pressure-sensitive adhesives are disclosed in *Handbook of Pressure-Sensitive Adhesive Technology*, D. Satas, pp. 370–403 (Van Nostrand Reinhold Co., 1982), which is hereby incorporated by reference. Preferably, the liner is coated with fluorocarbon diacrylate or a polymeric organic silicon material, more commonly referred to as a silicone. Silicones are preferred because silicones are commonly used, relatively inexpensive, and stable in most applications.

Although both surfaces of the removable liner or liners may be coated with a release coating, this is not a requirement of the present invention. However, if the removable liner(s) have a release coating on only one side, the liner(s) are preferably folded such that the release coating surface is facing outward, i.e. towards the reusable and disposable components. If the liners are coated on only the outer surface, the preferred removal process of liner assembly 70 in FIG. 10 involves first the removal of liner 50 by pulling grasping means 52. Subsequently, tab 62 may be pulled in order to remove liner 60. This sequence of liner removal minimizes the potential for the sticking of the non-coated liner surfaces to the adhesive during the removal process.

One method of measuring the adhesion between the liner and adhesive coating involves first cutting liner/adhesive sample strips about 2 cm wide, and at least 4 inches long. Then, the liner and adhesive are manually separated at one end of the sample. The separated edge of the liner is attached to a stationary jaw of a tensile testing apparatus, such as a model 1122 tensile tester, available from Instron Corp., Canton, Mass. The separated edge of the adhesive is placed in an opposing movable jaw of the tensile testing apparatus. Force is applied to the movable jaw by moving the movable jaw at a nearly constant rate, e.g. 1000 mm/min. in a direction opposite the stationary jaw. The separation force is typically recorded in terms of grams and normalized by dividing by sample width. The adhesion between the liner and the adhesive material may range from about 5 to about 100 grams per centimeter of liner width. More preferably, the force between liner and adhesive is about 5 to about 50 grams/cm liner width. The most preferred range of adhesionve to liner is about 5 to about 10 g/cm liner width.

Adhesives suitable for affixing the reusable component 2 to the disposable component 4 of the present invention include, without limitation, pressure sensitive adhesives such as polyacrylates, polyvinyl ethers, silicones, natural rubber, styrene-butadiene copolymers, styrene-isoprene copolymers, butyl rubber blended with polyisobutylene, butadiene-acrylonitrile rubbers, polychloroprene latex, polyurethanes, poly(vinyl pyrrolidone)s, vinyl pyrrolidone copolymers, ethylene vinyl acetates, and mixtures thereof. A more complete discussion of pressure-sensitive adhesives appears in *Handbook of Pressure-Sensitive Adhesive Technology*, D. Satas (Van Nostrand Reinhold Company, 1982), which is incorporated herein by reference. In addition to moderate adhesive strengths, biocompatibility is a desirable adhesive characteristic. A more preferred group of adhesives for securing the components of the electrotransport device to one another includes silicones, polyacrylates, and polyisobutylenes.

The thickness of the adhesive coating which secures the reusable component to the disposable component depends on a multitude of factors, including adhesive composition, the compositions of the surfaces which the adhesive contacts, desired adhesion and whether both components have an adhesive coating. Generally, the adhesive coating thickness ranges from about 0.025 mm to about 0.1 mm. More preferably, the adhesive coating thickness is about 0.4 mm to about 0.65 mm.

The removable liner of the present invention may be composed of a variety of materials. Preferably, the liner does not adhere strongly to the adhesive surface of either the disposable component and/or reusable component. A strong adhesion between the liner and the adhesive will cause the patient or user to experience difficulty in manually removing the liner. On the other hand, some adhesion between the liner and either disposable component or reusable component is required to hold the liner in place during manufacture, packaging, shipping and during the initial alignment step of the device assembly process.

Suitable liner materials include, without limitation, polyesters, polyethylenes, poly(vinyl chloride)s, polypropylenes, polystyrenes, polyacrylonitriles, paper, cloth or fabric, and the like and combinations thereof. Some polymer materials, such as polyethylenes, may benefit from addition of mesh or scrim to add strength. Polyesters are more preferable liner materials, while the most preferred polyester is poly(ethylene terephthalate). Poly(ethylene terephthalate) is available commercially from 3M Corporation, Minneapolis, Minn.

In addition, the thickness of the liner should be minimized while maintaining sufficient strength to prevent tearing upon removal. Thus, the required liner thickness is dependent upon the strength of the liner material and the adhesive force between the liner and the adhesive on disposable component and/or reusable component. The liner thickness preferably ranges from about 0.01 mm to about 0.25 mm. More preferably, the liner thickness is from about 0.025 mm to about 0.1 mm. Most preferably, the liner thickness ranges from about 0.06 mm to about 0.09 mm.

The shape and dimensions of the removable liner are a function of the shape and dimensions of the component, or larger of the components, which have an adhesive coating thereon which faces the other component. Preferably, components 2 and 4 have the same general size and shape. In addition, the removable liner is preferably sized to generally conform to the shape and size of the disposable and reusable components, with the exception of the grasping means as discussed above. However, the removable liner may extend beyond the edges of the components without causing significant problems. While the removable liner is not required to conform exactly to the size and shape of the reusable and disposable components, preferably the liner covers substantially all the adhesive coating or coatings of the components in order to prevent any premature adhesion.

The electrodes of the present invention are composed of an electrically conductive material such as a metal. For example, the electrodes may be formed from metal foil, metal screen, metal deposited or painted on a suitable backing, calendaring, film evaporation, or by embedding a metal powder in a binder matrix. Examples of suitable metals include silver, zinc, silver chloride, aluminum, platinum, stainless steel, gold, and titanium. For example, the anodic electrode may be composed of silver, while the cathodic electrode may be composed of silver chloride.

Alternatively, the electrodes may be formed of a polymer matrix containing a conductive filler such as a metal powder, powdered graphite, carbon fibers, or other electrically conductive filler material. The polymer-based electrodes may be produced by mixing the conductive filler in a polymer matrix, preferably a hydrophobic polymer matrix in order to minimize interaction with any water present in the reservoirs.

In the preferred embodiment of the invention, the reusable component contains both a power source and control circuitry. The controller may allow manual or automatic feedback adjustment of current fed to the electrodes. Yet, the invention contemplates those electrotransport systems wherein the reusable component contains a power source without a controlling component. In this system, the agent delivery would be initiated once the agent-transmitting surface of the assembled device was contacted with a body surface. Alternatively, the reusable component may contain only control circuitry, while the power source is located in the disposable component. An example of this would be an electrotransport system is powered by entirely by a galvanic couple, wherein power is generated by two dissimilar electrodes.

In the event the counter and donor electrodes are of dissimilar metals or have different half cell reactions, the electrodes themselves may generate at least a portion of the electrical power used to deliver the beneficial agent. When a galvanic couple is used, the donor electrode and counter electrode are integral portions of the power generating process. Such a galvanic couple powered system, absent some controlling means, activates automatically when body tissue and/or fluids form a complete circuit with the system. There exist numerous other examples of galvanic couple systems potentially useful in the present invention. Standard electrochemical reactions and the respective reduction potentials are well known in the art. For instance, see the CRC Handbook of Chemistry and Physics, pp. D133–D138, $62^{nd}$ edition (1981–1982), which is incorporated herein by reference.

Preferably the electrotransport devices of the present invention use a separate electrical power source, apart from the power generated by way of the electrodes forming a galvanic couple. Such a power source is typically a battery or plurality of batteries, connected in series or in parallel, and positioned electrically between the counter electrode and donor electrode, such that the donor electrode is connected to one pole of the power source and the counter electrode is connected to the opposite pole. Typically, one or more 3 volt button cell batteries, such as PANASONIC ® model CR 2025, are suitable to power electrotransport devices.

As mentioned above, the reusable component may include electronic circuitry for controlling the operation of the electrotransport device. Thus, the power source may include circuitry designed to permit the patient to manually turn the system on and off, such as with an on-demand medication regime, or to turn the system on and off at some desired periodicity, for example, to match the natural or circadian patterns of the body. A relatively simple controller or microprocessor could control the current as a function of time or could generate complex current waveforms such as pulses or sinusoidal waves. The control circuitry may also include a biosensor and some type of feedback system which monitors biosignals, provides an assessment of therapy, and adjusts the drug delivery accordingly. A typical example is the monitoring of the blood sugar level for controlled administration of insulin.

The donor reservoir and optional counter reservoir can be any material adapted to absorb and hold a sufficient quantity of liquid therein in order to permit transport of agent therethrough by iontophoresis. For example, gauzes, pads or sponges composed of cotton or other absorbent fabric, both natural and synthetic, may be used. More preferably, the matrices of the reservoirs are composed, at least in part, of hydrophilic polymer material. Hydrophilic polymer is typically preferred because water is the preferred ion transport medium, and hydrophilic polymers have a relatively high equilibrium water content. Most preferably, the matrices of the reservoirs are solid polymer matrices composed, at least in part, of insoluble hydrophilic polymer. Insoluble hydrophilic polymer matrices are sometimes preferred for structural reasons over soluble hydrophilic polymers. However, it should be noted that hydrophobic polymers having a microporous structure sufficient to enable ion transport may be utilized in the agent reservoirs.

The matrices can be crosslinked with the agent components in place such as a silastic matrix, or the polymers can be prefabricated and sorbed with the components from solutions as is the case with cellulose, woven fiber pads and sponges. The agent reservoirs can alternately be a gel matrix structure, formed similarly to the polymeric matrix structure, wherein the gel is formed of a hydrophilic polymer which is swellable or soluble in water. Such polymers can be blended with the components in any ratio, but preferably represent from a few percent up to about 50 percent by weight of the reservoir. The polymers can be linear or cross-linked. Suitable hydrophilic polymers include copolyesters such as HYTREL (DuPont De Nemours & Co., Wilmington, Del.), polyvinylpyrrolidones, polyvinyl alcohol, polyethylene oxides such as POLYOX (Union Carbide Corp.), CARBOPOL (BF Goodrich of Akron, Ohio), blends of polyoxyethylene or polyethylene glycols with polyacrylic acid such as POLYOX blended with CARBOPOL, polyacrylamide, KLUCEL, cross-linked dextran such as SEPHADEX (Pharmacia Fine Chemicals, AB, Uppsala, Sweden), WATER LOCK (Grain Processing Corp., Muscatine, Iowa) which is a starch-graft-poly(sodium acrylate-co-acrylamide) polymer, cellulose derivatives such as hydroxyethyl cellulose, hydroxypropylmethylcellulose, low-substituted hydroxypropylcellulose, and cross-linked Na-carboxymethylcellulose such as Ac-Di-Sol (FMC Corp., Philadelphia, Pa.), hydrogels such as polyhydroxyethyl methacrylate (National Patent Development Corp.), natural gums, chitosan, pectin, starch, guar gum, locust bean gum, and the like, along with blends thereof. Of these, polyvinylpyrrolidones are preferred. This list is merely exemplary of the materials suited for use in this invention. Other suitable hydrophilic polymers can be found in J. R. Scott & W. J. Roff, Handbook of Common Polymers (CRC Press, 1971), which is hereby incorporated by reference.

Optionally, the matrices of the reservoirs 16 and 18 may contain a hydrophobic polymer for enhanced structural rigidity. Preferably the hydrophobic polymer is heat fusible, in order to improve the lamination of the reservoirs to adjacent components, such as the insulator or a rate controlling membrane. Suitable hydrophobic polymers for use in the reservoir matrices include, but are not limited to, polyisobutylenes, polyethylene, polypropylene, polyisoprenes and polyalkenes, rubbers, copolymers such as KRATON, polyvinylacetate, ethylene vinyl acetate copolymers, polyamides such as nylons, polyurethanes, polyvinylchloride, acrylic or methacrylic resins such as polymers of esters of acrylic or methacrylic acid with alcohols such as n-butanol, 1-methyl pentanol, 2-methyl pentanol, 3-methyl pentanol, 2-ethyl butanol, isooctanol, n-decanol, alone or copolymerized with ethylenically unsaturated monomers such as acrylic acid, methacrylic acid, acrylamide, methacrylamide, N-alkoxymethyl acrylamides, N-alkoxymethyl methacrylamides, N-tert-butylacrylamide, itaconic acid, N-branched alkyl maleamic acids wherein the alkyl group has 10–24 carbon atoms, glycol diacrylates, and blends thereof. Most of the above-mentioned hydrophobic polymers are heat fusible. Of these, polyisobutylenes are preferred.

The reservoir matrices may be a polymeric matrix structure formed by blending the desired agent, drug, electrolyte, or other component(s), with an inert polymer by such processes as melt blending, solvent casting, or extrusion. Typically, the donor reservoir contains a agent to be delivered, while the counter reservoir contains an electrolyte, e.g. a water soluble biocompatible salt, such as sodium chloride. In addition to the agent and electrolyte, the reservoirs may also contain other conventional materials such as dyes, pigments, inert fillers, and the like.

This invention has utility in connection with the delivery of agents within the broad class deliverable through body surfaces, including skin, mucosa, and nails. The expressions "drug" and "agent" are used interchangeably herein and are intended to have their broadest interpretation as any substance which is delivered to a living organism to produce a desired, usually beneficial, effect. In general, this includes therapeutic agents in all of the major therapeutic areas including, but not limited to, anti-infectives such as antibiotics and antiviral agents, analgesics including fentanyl, sufentanil, buprenorphine and analgesic combinations, anesthetics, anorexics, antiarthritics, antiasthmatic agents such as terbutaline, anticonvulsants, antidepressants, antidiabetic agents, antidiarrheals, antihistamines, anti-inflammatory agents, antimigraine preparations, antimotion sickness preparations such as scopolamine and ondansetron, antinauseants, antineoplastics, antiparkinsonism drugs, antipruritics, antipsychotics, antipyretics, antispasmodics, including gastrointestinal and urinary, anticholinergics, antiulceratives such as ranitidine, sympathomimetrics, xanthine derivatives, cardiovascular preparations including calcium channel blockers such as nifedipene, beta-blockers, beta-agonists such as dobutamine and ritodrine, antiarrythmics, antihypertensives such as atenolol, ACE inhibitors such as enalapril, benzodiazepine antagonists such as flumazenil, diuretics, vasodilators, including general, coronary, peripheral and cerebral, central nervous system stimulants, cough and cold preparations, decongestants, diagnostics, hormones such as parathyroid hormone, hypnotics, immunosuppressives, muscle relaxants, parasympatholytics, parasympathomimetrics, prostaglandins, proteins, peptides, psychostimulants, sedatives and tranquilizers.

The invention is also useful in the controlled delivery of peptides, polypeptides, proteins and other macromolecules. These macromolecular substances typically have a molecular weight of at least about 300 daltons, and more typically a molecular weight in the range of about 300 to 40,000 daltons. Specific examples of peptides, and proteins and macromolecules in this size range include, without limitation, LHRH, LHRH analogs such as buserelin, gonadorelin, napharelin and leuprolide, GHRH, GHRF, insulin, insulotropin, heparin, calcitonin, octreotide, endorphin, TRH, NT-36 (chemical name: N=[[(s)-4-oxo-2-azetidinyl]carbonyl]-L-histidyl-L-prolinamide), liprecin, pituitary hormones (e.g., HGH, HMG, HCG, desmopressin acetate, etc.), follicle luteoids, $\alpha$ANF, growth factors such as growth factor releasing factor (GFRF), $\beta$MSH, somatostatin, atrial natriuretic peptide, bradykinin, somatotropin, platelet-derived growth factor, asparaginase, bleomycin sulfate, chymopapain, cholecystokinin, chorionic gonadotropin, corticotropin (ACTH), epidermal growth factor, erythropoietin, epoprostenol (platelet aggregation inhibitor), follicle stimulating hormone, glucagon, hirulog, hyaluronidase, interferon, insulin-like growth factors, interleukin-1, interleukin-2, menotropins (urofollitropin (FSH) and LH), oxytocin, streptokinase, tissue plasminogen activator, urokinase, vasopressin, desmopressin, ACTH analogs, ANP, ANP clearance inhibitors, angiotensin II antagonists, antidiuretic hormone agonists, antidiuretic hormone antagonists, bradykinin antagonists, CD4, ceredase, CSF's, enkephalins, FAB fragments, IgE peptide suppressors, IGF-1, neuropeptide Y, neurotrophic factors, oligodeoxynucleotides and their analogues such as antisense RNA, antisense DNA and anti-gene nucleic acids, opiate peptides, colony stimulating factors, parathyroid hormone and agonists, parathyroid hormone antagonists, prostaglandin antagonists, pentigetide, protein C, protein S, ramoplanin, renin inhibitors, thymosin alpha-1, thrombolytics, TNF, vaccines, vasopressin antagonist analogs, alpha-1 anti-trypsin (recombinant), and TGF-beta.

In particular, the present invention has particular utility in delivering drugs whose delivery rate is dependent upon the physical activity of a patient. Specific examples of such drugs and the corresponding patient motion or activity include the following: delivery of theophylline or epinephrine for the treatment of apnea; delivery of an antitussive such as dextromethorphan for the treatment of coughing; delivery of an anticonvulsant for the treatment of an epileptic seizure; delivery of insulin based upon the level of patient activity (e.g., lower insulin delivery rate for more vigorous levels of patient activity); delivery of antiparkinson agent in response to patient shaking; delivery of antispasmodics such as diazepam for treatment of muscle spasms; and delivery of an antiemetic such as scopolamine or meclizine, in response to motion, for the treatment of motion sickness.

Having thus generally described our invention and described in detail certain preferred embodiments thereof, it will be readily apparent that various modifications to the invention may be made by workers skilled in the art without departing from the scope of this invention, which is limited only by the following claims.

What is claimed is:

1. An electrotransport device for delivering an agent through a body surface, comprising:
    (a) a reusable component containing electronic circuitry for performing at least one of (i) generating and (ii) controlling electric current applied by the device, the reusable component having a mating surface;
    (b) a disposable component containing the agent to be delivered and having a mating surface adapted to mate to said reusable component mating surface, the mating surfaces being capable of adhering to one another in a plurality of orientations, at least one of which is a desired mating orientation;
    (c) means, on at least one of the reusable component and the disposable component, for aligning said reusable component into said desired mating orientation with said disposable component; and
    (d) at least one removable liner interposed between said component mating surfaces during component alignment, said liner preventing said mating surfaces from adhering to one another during component alignment, said liner being removable from between the aligned mating surfaces without disturbing said desired mating orientation.

2. An electrotransport device as recited in claim 1, further comprising means for electrically connecting the components.

3. An electrotransport device as recited in claim 2, further comprising means for mechanically connecting the components.

4. An electrotransport device as recited in claim 1, wherein said aligning means further provides a function chosen from the group consisting of mechanically connecting said components, electrically connecting said components, and a combination thereof.

5. An electrotransport device as recited in claim 4, wherein said aligning means are mating electrically conductive snap connectors.

6. An electrotransport device as recited in claim 1, wherein said removable liner comprises a flexible sheet of material folded upon itself, thereby forming a fold axis, said folded flexible sheet having a first surface adjacent to an adhesive mating surface and a second surface adjacent to said other mating surface.

7. An electrotransport device as recited in claim 6, wherein said liner is provided with a grasping means by which said liner may be manually removed.

8. An electrotransport device as recited in claim 7, wherein said grasping means comprises a tab which extends beyond a peripheral edge of said components when said components are aligned.

9. An electrotransport device as recited in claim 7, wherein said liner is provided with access means through which said aligning means extends when said components are aligned.

10. An electrotransport device as recited in claim 9, wherein said access means comprises at least one hole through said liner.

11. An electrotransport device as recited in claim 10, wherein said access means comprises four holes through said liner, said liner having two substantially parallel lines of perforations extending between said holes on opposite sides of the fold axis, wherein said holes on opposite sides of the fold axis are essentially equidistant from the fold axis, and wherein said aligning means extend through said holes.

12. An electrotransport device as recited in claim 10, wherein said access means comprises two elongated openings through said liner, said elongated openings each having an axis which is substantially perpendicular to the fold axis, wherein portions of said elongated openings on either side of the fold axis are substantially similar in size and shape, and wherein said aligning means extend through said openings.

13. An electrotransport device as recited in claim 1, wherein said device comprises a first removable liner and a second removable liner, said first liner comprising a flexible sheet of material folded onto itself and having a first grasping means by which said first liner may be manually removed, said second liner comprising a flexible sheet of material folded onto itself and having a second grasping means by which said second liner may be manually removed, wherein said liners are shaped and positioned such that access is provided for said aligning means to extend therethrough while said liners are positioned between said components.

14. An electrotransport device as recited in claim 1, wherein said disposable component mating surface has an adhesive means disposed thereon and said removable liner is releasably affixed thereto prior to said component alignment.

15. An electrotransport device as recited in claim 6, wherein the adhesion between said removable liner and said adhesive mating surface is about 5 to about 50 grams per centimeter of said removable liner.

16. An electrotransport device as recited in claim 6, wherein the adhesion between said removable liner and said adhesive mating surface is about 5 to about 10 grams per centimeter of said removable liner.

17. An electrotransport device as recited in claim 6, wherein said removable liner is coated with a release coating on at least one surface.

18. An electrotransport device as recited in claim 17, wherein said release coating surface faces said component mating surfaces.

19. An electrotransport device as recited in claim 1, said reusable component comprising (i) a power source and (ii) electrical control circuitry in electrical contact with said power source, said disposable component comprising (i) a donor electrode in electrical contact with a donor reservoir including said agent, separated by insulating means from (ii) a counter electrode in electrical contact with a counter reservoir, said disposable component further comprising an adhesive mating surface having said removable liner releasably affixed thereto, wherein said aligning means are mating metallic snap connectors affixed to said components, said snap connectors providing electrical and mechanical connecting of said components.

20. A disposable assembly for use in conjunction with a reusable component to form an electrotransport agent delivery device, said disposable assembly comprising:

(a) a disposable component containing the agent to be delivered and having a mating surface adapted to mate with a mating surface on said reusable component, said reusable component containing electronic circuitry for performing at least one of (i) generating and (ii) controlling electric current applied by the device, said disposable component mating surface having adherent properties, said reusable and disposable components being capable of adhering to one another in a plurality of orientations, at least one of which is a desired mating orientation;

(b) means on at least one of the reusable component and the disposable component for aligning said components in the desired mating orientation; and (c) at least one removable liner disposed on said adherent mating surface, said liner preventing said mating surfaces from adhering to one another during component alignment, said liner being removable from between the aligned mating surfaces without disturbing said desired mating orientation.

21. The assembly of claim 20, wherein said removable liner comprises a flexible sheet of material folded upon itself, thereby forming a fold axis, said folded flexible sheet having a first surface disposed on said adherent mating surface and a second surface adjacent to said other mating surface during component alignment.

22. The assembly of claim 20, wherein said liner is provided with a grasping means by which said liner may be manually removed.

23. The assembly of claim 20, wherein said liner is provided with access means through which said aligning means extends when said components are aligned.

24. The assembly of claim 23, wherein said access means comprises at least one opening through said liner.

25. The assembly of claim 24, wherein said opening comprises four holes through said liner, said liner having two substantially parallel lines of perforations extending between said holes on opposite sides of the fold axis, wherein said holes on opposite sides of the fold axis are essentially equidistant from the fold axis, and wherein said aligning means extend through said holes.

26. The assembly of claim 24, wherein said opening comprises two elongated openings through said liner, said elongated openings each having an axis which is substantially perpendicular to the fold axis, wherein portions of said elongated openings on either side of the fold axis are substantially similar in size and shape, and wherein said aligning means extend through said openings.

27. The assembly of claim 24, wherein said device comprises a first and a second removable liner, said first liner comprising a flexible sheet of material folded onto itself and having a first grasping means by which said first liner may be manually removed, said second liner comprising a flexible sheet of material folded onto itself and having a second grasping means by which said second liner may be manually removed, wherein said liners are shaped and positioned such that access is provided for said aligning means to extend therethrough while said liners are positioned between said components.

28. A method of mating a reusable component to a disposable component to form an electrotransport agent delivery, device, comprising:

(1) placing the agent to be delivered in the disposable component;

(2) placing electronic circuitry, for performing at least one of (i) generating and (ii) controlling electric current applied by the device, in the reusable component;
(3) placing a removable liner on at least one adhesive mating surface of said reusable and disposable components, said component mating surfaces being capable of adhering to one another in a plurality of orientations, at least one of which is a desired mating orientation;
(4) aligning said components, by way of an aligning means on at least one of the reusable component and the disposable component, in said desired mating orientation with said liner interposed between said mating surfaces; and
(5) removing said removable liner from between the aligned mating surfaces without disturbing said desired mating orientation, thereby adhesively mating said components to one another.

29. A method as recited in claim 28, further comprising mechanically connecting said components prior to removing said removable liner.

30. A method as recited in claim 29, wherein said step of mechanically connecting said components further provides electrical connection of electrodes to a power source.

31. A method as recited in claim 28, wherein said aligning further provides a function chosen from the group consisting of mechanically connecting said components, electrically connecting said components, and a combination thereof.

32. A method as recited in claim 28, further comprising folding a sheet of liner material onto itself, thereby forming said removable liner.

33. A method as recited in claim 32, further comprising providing said removable liner with access means whereby aligning means may pass therethrough.

* * * * *